United States Patent [19]

Matsumoto

[11] Patent Number: 5,394,240
[45] Date of Patent: Feb. 28, 1995

[54] HIGH-ACCURACY AIR REFRACTOMETER UTILIZING TWO NONLINEAR OPTICAL CRYSTAL PRODUCING 1ST AND 2ND SECOND-HARMONIC-WAVES

[75] Inventor: Hirokazu Matsumoto, Tsukuba, Japan

[73] Assignees: Agency of Industrial Science & Technology; Ministry of International Trade & Industry, both of Tokyo, Japan

[21] Appl. No.: 187,483

[22] Filed: Jan. 28, 1994

[30] Foreign Application Priority Data

Feb. 2, 1993 [JP] Japan ................................. 5-037529

[51] Int. Cl.$^6$ ............................................ G01B 11/02
[52] U.S. Cl. .................................. 356/349; 356/361; 356/358
[58] Field of Search ............... 356/128, 345, 349, 351, 356/358, 361

[56] References Cited

U.S. PATENT DOCUMENTS 5,116,126  5/1992  Wang et al. ......................... 356/349
5,172,186  12/1992 Hosoe ................................ 356/358
5,177,566  1/1993  Leuchs et al. ..................... 356/358
5,337,145  8/1994  Chaney .............................. 356/358

Primary Examiner—Samuel A. Turner
Assistant Examiner—Russell C. Wolfe
Attorney, Agent, or Firm—Oblon, Spivak, McClelland, Maier, & Neustadt

[57] ABSTRACT

An air refractometer measures the refractive index of air by directing a laser beam onto a first nonlinear optical crystal to convert a part thereof into a second-harmonic wave, directs the laser beam and the second-harmonic wave onto a reflecting mirror which reflects them onto a second nonlinear optical crystal to convert another part of the laser beam into a second-harmonic wave, produces interference fringes by interference between the harmonic wave produced by the first nonlinear optical crystal and the harmonic wave produced by the second nonlinear optical crystal, counts the number of interference fringes generated when the reflecting mirror is moved, and divides the number of interference fringes by the distance moved by the reflecting mirror.

3 Claims, 2 Drawing Sheets

HIGH-ACCURACY AIR REFRACTOMETER UTILIZING TWO NONLINEAR OPTICAL CRYSTAL PRODUCING 1ST AND 2ND SECOND-HARMONIC-WAVES

BACKGROUND OF THE INVENTION

1. Field of the Invention

This invention relates to an air refractometer able to measure the refractive index of air with high accuracy.

2. Description of the Prior Art

Recent advances in scientific and industrial technology have created a need for high-accuracy length measurement. Optical methods are useful for noncontact and high-accuracy measurements because they achieve high-accuracy measurement without touching the objects between which the measurement is made. The interferometric method is particularly well adapted for measuring lengths with high relative accuracy. It has a problem, however, in that the optical wavelengths are affected on the $10^{-6}$ order by the refractive index of the air in which the measurement is conducted.

For overcoming this problem, the inventors previously proposed a two-color method for measuring geometric lengths, specifically a method of measurement using two laser beams of different colors, i.e. different wavelengths, as the light sources of a length-measuring interferometer, thus enabling length values optically measured by optical interference to be corrected in real time for the refractive index of the surrounding air.

In the length-measuring interferometer based on this two-color method a laser beam is directed onto a nonlinear crystal which, as a result, produces a second-harmonic wave. The second-harmonic wave is separated out, and the fundamental wave and the second-harmonic wave are separately used to generate interference fringes. The difference in the number of interference fringes is then determined. If the wavelength of the fundamental laser beam is defined as $\lambda_1$, the wavelength of the second-harmonic wave as $\lambda_2$, the length values optically measured using the fundamental laser beam and the second-harmonic wave as $L_1$ and $L_2$, respectively, and the indices of refraction of the air at $\lambda_1$ and $\lambda_2$ as $n_1$ and $n_2$, respectively then the refractive index $n_2$ of the air with respect to the second-harmonic wave can be expressed as $$n_2 = 1 + (L_1 - L_2) \cdot A / L_x \qquad (1)$$

In this equation, $L_x$ is the value of the measured interval and since an approximate value suffices can be replaced with the measured length value $L_1$ or $L_2$. "A" is a coefficient and, as is well known, is a constant given by $\{(n_{02}-1)/(n_{02}-n_{01})\}$, where $n_{01}$ and $n_{02}$ are the refractive indices of air under standard conditions. The value of the coefficient A is dependent on the two wavelengths used and has a value in the range of several tens to several hundreds. As a result, the resolution of the air refractive index measurement by the two-color method employed by the length-measuring interferometer is poor. It is therefore difficult to achieve improved measurement accuracy by optical interference in the relatively short length range between several tens and several hundreds of centimeters.

Moreover, since the conventional length-measuring interferometer using the two-color method requires the interference fringes formed using light of two wavelengths to be separately detected and counted photoelectrically, it not only has poor fringe measurement resolution but also requires a complex measurement systems owing to its need to employ highly coherent light sources etc.

The object of the invention is to overcome the drawbacks of the conventional two-color length-measuring interferometer by providing an air refractometer of simple configuration that is able to measure the index of refraction of air with high accuracy.

SUMMARY OF THE INVENTION

For achieving this object, the present invention provides a high-accuracy air interferometer comprising a laser beam source for emitting a laser beam, a first nonlinear optical crystal for receiving the laser beam from the laser beam source and converting a part thereof into a second-harmonic wave, a reflecting mirror for reflecting the laser beam and the second-harmonic wave, a conveyance means for conveying the reflecting mirror, a second nonlinear optical crystal for receiving the laser beam and the second-harmonic wave reflected by the reflecting mirror and converting a part of the laser beam into a second-harmonic wave, and means for producing interference fringes by interference between the second-harmonic wave produced by the first nonlinear optical crystal and the second-harmonic wave produced by the second nonlinear optical crystal.

If the air refractive indices at wavelengths $\lambda_1$ and $\lambda_2$ are $n_1$ and $n_2$, the difference in optical path length $\Delta L$ in the interference between the second-harmonic wave propagated after conversion to wavelength $\lambda_2$ by the first nonlinear optical crystal and the light wave converted to wavelength $\lambda_2$ by the second nonlinear optical crystal after being propagated without change can be expressed as $$\Delta L = L (n_2 - n_1) = (n_2 - 1) L/A \qquad (2)$$

where L is the geometrical length when the reflecting mirror moves and need only be an approximate value. The air refractive index can therefore be obtained by measuring the difference in optical path length $\Delta L$, namely the phases of the interference fringes, dividing the measured value by optical path length $L_1$ or $L_2$ instead of by the geometric length L, and multiplying the result by the coefficient A. As can be seen from Eq. (2), the present invention requires measurement of only the extremely short difference in optical path length $\Delta L$. Since the phases of the interference fringes can therefore be counted with high resolution, the air refractive index can be determined with high accuracy.

The above and other features of the present invention will become apparent from the following description made with reference to the drawings.

DESCRIPTION OF THE PREFERRED EMBODIMENT

Figure 1:
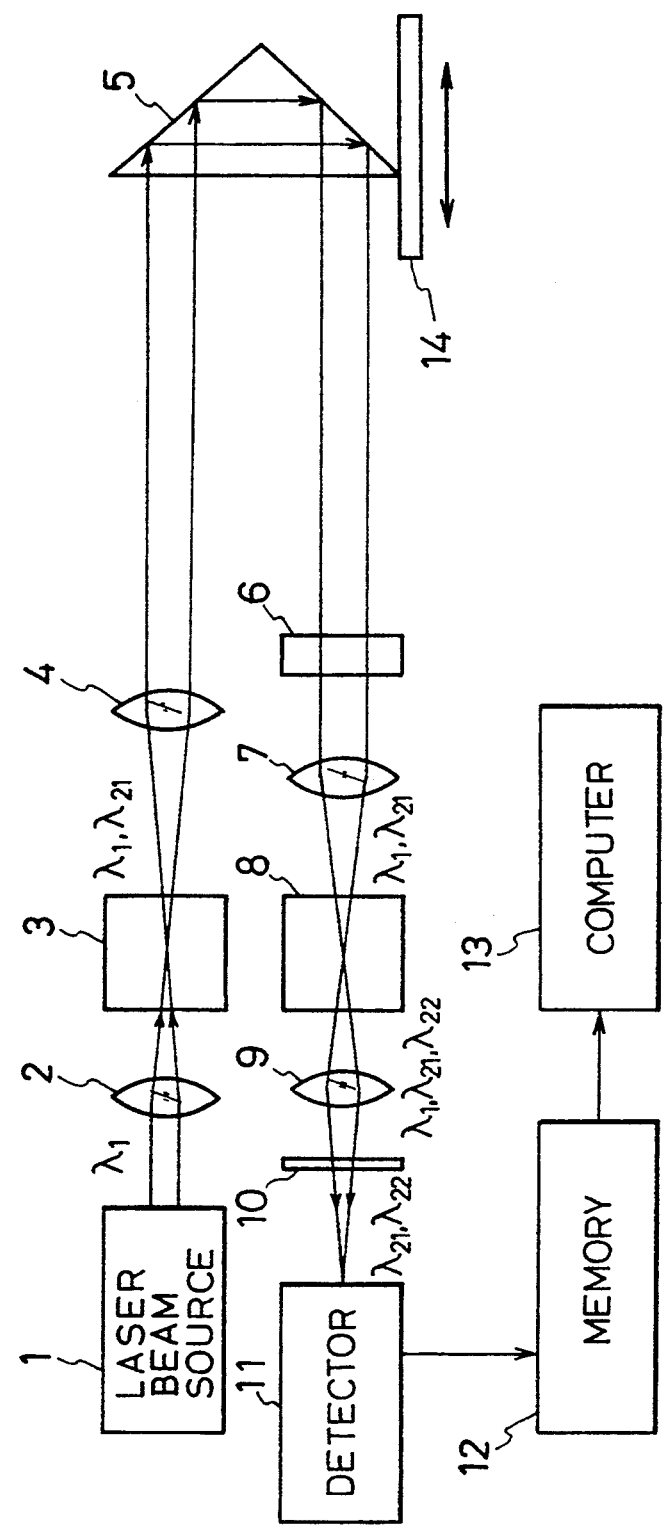
FIG. 1 is a schematic view of an embodiment of the high-accuracy air refractometer according to the present invention.

FIG. 1 is a schematic view showing the configuration of an embodiment of the high-accuracy air refractometer according to the present invention. The refractometer comprises a laser beam source 1, a lens 2 and a first nonlinear crystal 3 positioned in order on the optical axis of the laser beam source 1, and a lens 4 and a reflecting mirror 5 positioned in order on the optical axis of the light emitting side of the first nonlinear crystal 3. The reflecting mirror 5 is mounted on a conveyance means 14 powered by a stepper or the like for conveying the reflecting mirror 5 at a prescribed velocity in the direction of the optical axis. On the light emitting optical axis of the reflecting mirror 5 are positioned in order a half-wave plate 6, a lens 7, a second nonlinear crystal 8, a lens 9, a filter 10 and a photoelectric detector 11. The photoelectric detector 11 is electrically connected with a memory 12 and a personal computer 13.

In the so-configured air refractometer, a laser beam of wavelength $\lambda_1$ emitted by the laser beam source 1 is focused on the first nonlinear crystal 3 by the lens 2. As the first nonlinear crystal 3 there can be used a KTiOPO$_4$ crystal or other such known second-harmonic wave producing crystal of arbitrary size.

A part of the laser beam received by the first nonlinear crystal 3 is converted into a second-harmonic wave ($\lambda_{21}$) which after being collimated by the lens 4 propagates through the air to the reflecting mirror 5. After having its polarization state adjusted by the half-wave plate 6, the light reflected by the reflecting mirror 5 passes through the lens 7 to the second nonlinear crystal 8.

The wavelength $\lambda_{21}$ of the second-harmonic wave produced by the first nonlinear crystal 3 is shorter than the wavelength $\lambda_1$ of the fundamental laser beam. Since it therefore has a larger refractive index, it propagates through the air more slowly. The fundamental laser beam thus arrives earlier at the second nonlinear crystal 8 and the second nonlinear crystal 8 converts a part thereof into a second-harmonic wave ($\lambda_{22}$). The second-harmonic wave $\lambda_{21}$ produced by the first nonlinear crystal 3 advances as is to the second nonlinear crystal 8 and interference thus arises between it and the second-harmonic wave $\lambda_{22}$ produced by the second nonlinear crystal 8. The waves then advance through the lens 9 to the filter 10 which removes the fundamental laser beam $\lambda_1$ and the remaining waves pass to the photoelectric detector 11. When the reflecting mirror 5 is moved a given distance along the optical axis at a given velocity, therefore, interference fringes are formed in proportion to the distance moved. As in the case of the first nonlinear crystal, the second nonlinear crystal can also be a KTiOPO$_4$ crystal or other such second-harmonic wave producing crystal.

The photoelectric detector 11 can be a photodiode. Its output is stored in the memory 12 and the personal computer 13 first uses the stored information for calculating the number of interference fringes formed and then divides the result by the distance that the reflecting mirror 5 moved to obtain the refractive index of the air.

Figure 2:
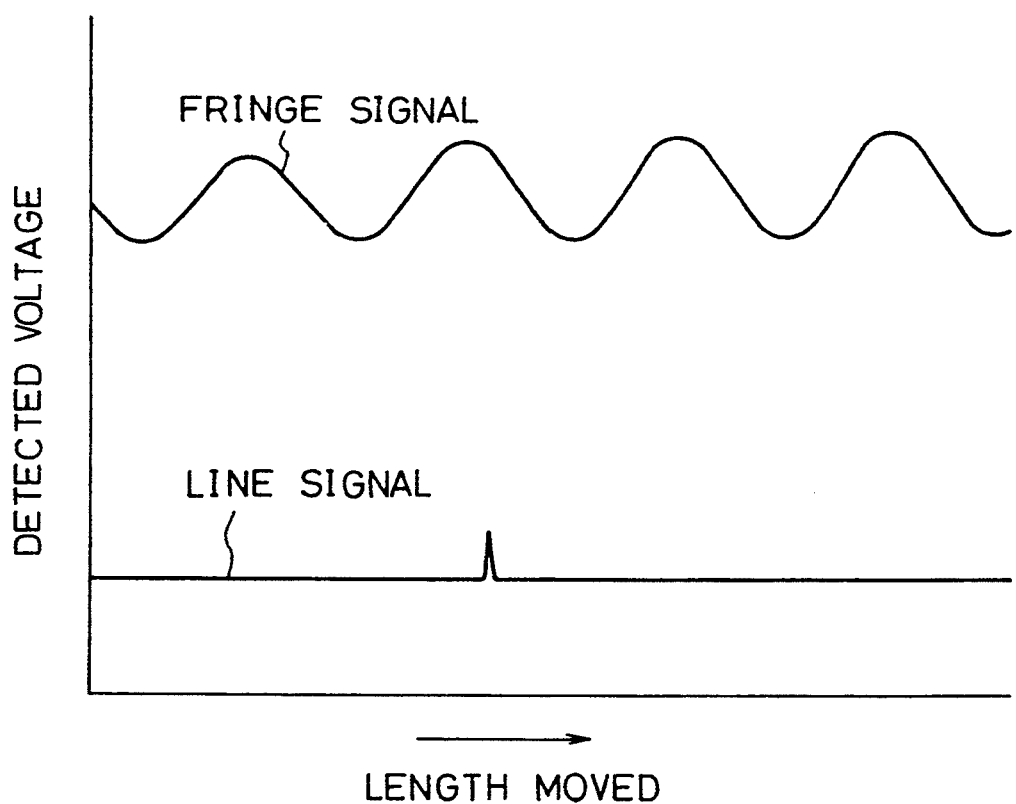
FIG. 2 is a graph showing an example of the interference-fringe signal obtained by an air refractometer according to the invention.

A working example of the invention will now be explained. An air refractometer of the configuration of FIG. 1 was fabricated using as the laser beam source 1 a 1.06 $\mu$m wavelength YAG laser with an output power of about 40 mW. The laser beam ($\lambda 1$) produced by the YAG laser was focused on a KTiOPO$_4$ crystal (type II) measuring 10 mm in length (the first nonlinear crystal 3) by an objective lens with a focal length of 60 mm (the lens 2) after adjusting the polarization state of the light by a half-wave plate in the laser system. As a result, the KTiOPO$_4$ crystal generated a second-harmonic wave ($\lambda_2 = 532$ nm) at an output power of about 4 $\mu$W. The fundamental and second-harmonic waves were collimated by an achromatic lens with a focal length of 150 mm (the lens 4), and the resulting beams, which measured about 5 mm in diameter, were allowed to propagate through the air to a corner-cube prism (the reflecting mirror 5) on a moving carriage (the conveyance means 14). The beams were reflected by the corner-cube prism while it was displaced along the optical axis by about 40 mm. The reflected beams then advanced to a second KTiOPO$_4$ crystal measuring 5 mm in length (the second nonlinear crystal 8) through a half-wave plate appropriate only for a wavelength of 1.06 $\mu$m (the half-wave plate 6) and an objective lens with a focal length of 60 mm (the lens 7). The second nonlinear crystal 8 converted only a part of the fundamental wave into a second-harmonic wave and did not modify the second-harmonic wave generated by the first nonlinear crystal 3. As a result, the second-harmonic waves generated by the first and second nonlinear crystals 3 and 8 generated interference fringes in accordance with the variation in the dispersion property of the air along the optical path of the refractometer. For detecting the interference fringes, the beams were passed through a condenser lens (the lens 9) and the filter 10 and focused on a photodiode (the photoelectric detector 11). The fringe signals produced by the photoelectric detector 11 were input to a signal-memory (the memory 12) and then analyzed to a phase resolution of 1° by the personal computer 13. FIG. 2 shows the interference-fringe signals when the corner-cube prism was conveyed at a velocity of about 2 mm/s. The S/N ratio was large enough for accurate determination of the phase. The line signal shown is one from a line-detector for triggering the measuring system with the use of an auxiliary scale, as explained below.

The refractometer was used to measure the refractive index of air at travel distances of 43 and 64 cm in an underground tunnel with stable air conditions on different days. The distances were measured to an accuracy of 0.05 mm using an ordinary commercially available laser interferometer and line signals to trigger the measuring system. The line signals were generated by detecting the output power of a laser diode with photodiodes at two positions along the optical path of the refractometer and were input to the computer simultaneously with the interference-fringe signals. The temperature, pressure, and humidity of the air at a point along the optical path under measurement was measured simultaneously with meteorological sensors, with accuracies of 0.05° C., 15 Pa and 10%, respectively, and the refractive index was calculated to an accuracy of better than $1 \times 10^{-7}$. The measurement results are shown in Table 1 in comparison with results calculated using Edlen's formula. In the present method, the coefficient A was calculated to be 65.592 from Edlen's formula. The difference between the results by the present invention at a distance near 50 cm and those of Edlen's method is seen to be less than the experimental error of $1 \times 10^{-7}$. Although the invention gives an average refractive index along the entire travel path and Edlen's method gives the refractive index at one point, the results are comparable because the tunnel was under steady air condition at about 18.3° C., though the former is required in the length measurement.

TABLE 1

| Distance (cm) | Present method | Edlén's method | Difference |
| --- | --- | --- | --- |
| 40.1 | 276.54 | 276.25 | 0.29 |
|  | 276.29 | 276.25 | 0.04 |
| 42.4 | 276.48 | 276.32 | 0.16 |
| 63.5 | 273.12 | 273.04 | 0.08 |
|  | 276.10 | 275.93 | 0.17 |
|  | 276.01 | 275.74 | 0.27 |
|  | 275.38 | 275.44 | −0.06 |
| Average | 275.70 | 275.57 | 0.14 |

As explained in the foregoing, in the prior art length-measuring interferometer using the two-color method the fundamental wave and the second-harmonic wave are separately used to generate separate sets of interference fringes by means of beam splitters, the number of interference fringes in each set is counted, and the difference in the number of interference fringes in the two sets is determined. Because of this, the number of interference fringes generated is large and this makes it difficult to achieve an improvement in the interference measurement resolution. In contrast, the present invention uses the second nonlinear crystal in place of the beam splitter for generating interference fringes between two second-harmonic waves. As a result, only a number of interference fringes proportional to the difference in air refractive index at the wavelengths of the two waves are formed. Since this number is much smaller than in the conventional case, by a factor on the order of $10^{-6}$ to be specific, the interference fringes generated can be recorded at high density in a computer or the like. Since it is therefore possible to determine the number and phase of the interference fringes with high accuracy, length measurement can be conducted at a high accuracy on the nanometer order.

Length-measuring interferometers are currently used in a wide range of scientific and industrial fields. Already applied for improving the dimensional precision of components in the advanced electronic and machinery sectors, they are now being increasingly called upon to provide accurate length measurement in unstable environments and over long optical paths. For this it is necessary to overcome the problems of air fluctuation and enable correction for changes in the refractive index of air. Since the present invention enables automatic, real-time correction for air refractivity, it enables length measurement by optical interferometry to be conducted with high accuracy in air. As such, it can be expected to find extensive utilization in the optical measurement field.

The invention thus provides a novel length measurement technology with high utility as a method of air refractivity correction for use in conjunction with component and product high-accuracy dimensional measurement technology and high-accuracy calibration technology for other types of measurement equipment, in the production of semiconductor devices and other electronic products as well as in the machinery and other high-precision industrial fields.

What is claim is:

1. A high-accuracy air interferometer comprising a laser beam source for emitting a laser beam, a first nonlinear optical crystal for receiving the laser beam from the laser beam source and converting a part thereof into a first second-harmonic wave, a reflecting mirror for reflecting the laser beam and the first second-harmonic wave, a conveyance means for conveying the reflecting mirror, a second nonlinear optical crystal for receiving the laser beam and the first second-harmonic wave reflected by the reflecting mirror and converting a part of the laser beam into a second second-harmonic wave, means for producing interference fringes by interference between the first second-harmonic wave produced by the first nonlinear optical crystal and the second second-harmonic wave produced by the second nonlinear optical crystal, and means for counting the interference fringes and dividing the number of interference fringes counted by a distance moved by the reflecting mirror.

2. A high-accuracy air interferometer according to claim 1, further comprising a filter means positioned after the second nonlinear optical crystal for removing a part of the laser beam not converted into the first and second second-harmonic waves.

3. A high-accuracy air interferometer according to claim 1, further comprising a half-wave plate provided between said reflecting mirror and said second nonlinear optical crystal.

* * * * *